(12) United States Patent
Claypool et al.

(10) Patent No.: US 7,658,741 B2
(45) Date of Patent: Feb. 9, 2010

(54) MULTI-POSITIONABLE CUT GUIDE

(75) Inventors: Jody Claypool, Columbia City, IN (US); Maleata Y Hall, Warsaw, IN (US); Shawn E McGinley, Fort Wayne, IN (US); Sudip Hui, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 509 days.

(21) Appl. No.: 11/154,774

(22) Filed: Jun. 16, 2005

(65) Prior Publication Data
US 2007/0005073 A1 Jan. 4, 2007

(51) Int. Cl.
*A61F 5/00* (2006.01)
(52) U.S. Cl. .................. 606/87; 606/86 R; 606/88; 606/89
(58) Field of Classification Search .............. 606/87–89, 606/86 R
See application file for complete search history.

(56) References Cited

U.S. PATENT DOCUMENTS

| 5,122,144 | A | | 6/1992 | Bert et al. | |
|---|---|---|---|---|---|
| 5,209,750 | A | * | 5/1993 | Stef | 606/54 |
| 5,234,433 | A | | 8/1993 | Bert et al. | |
| 5,445,642 | A | | 8/1995 | McNulty et al. | |
| 5,474,559 | A | | 12/1995 | Bertin et al. | |
| 5,520,695 | A | | 5/1996 | Luckman | |
| 5,562,675 | A | | 10/1996 | McNulty et al. | |
| 5,653,714 | A | * | 8/1997 | Dietz et al. | 606/87 |
| 6,514,259 | B2 | * | 2/2003 | Picard et al. | 606/88 |
| 7,033,361 | B2 | * | 4/2006 | Collazo | 606/87 |
| 7,309,339 | B2 | * | 12/2007 | Cusick et al. | 606/88 |
| 2003/0171757 | A1 | * | 9/2003 | Coon et al. | 606/87 |
| 2005/0228393 | A1 | * | 10/2005 | Williams et al. | 606/87 |
| 2007/0173849 | A1 | * | 7/2007 | Claypool et al. | 606/87 |

OTHER PUBLICATIONS

Innex™ Knee System Surgical Technique Primary.

* cited by examiner

*Primary Examiner*—Eduardo C Robert
*Assistant Examiner*—Tara R George
(74) *Attorney, Agent, or Firm*—Baker & Daniels LLP

(57) ABSTRACT

A multi-positionable cut guide including a bone attachment device, base, and guide member. Bone attachment device is adapted to be coupled to the bone and has a base receiving portion. Base includes a mounting portion slideably coupled to base receiving portion such that base is slideable relative to attachment device along at least one dimension. Guide housing is pivotally mounted to base and guide member is rotatably mounted to guide housing. Guide member defines an axis about which it is rotatable. Guide member defines an elongated guide slot extending along the axis and adapted to receive and guide a saw for resecting the end of the bone. Guide slot defines a cut guide plane, the position of which is adjustable relative to the bone via sliding of base along at least one dimension, pivoting of the guide housing relative to base, and rotation of guide member about the axis.

12 Claims, 6 Drawing Sheets

MULTI-POSITIONABLE CUT GUIDE

BACKGROUND

The present invention relates to cut guides for resecting the end of a bone and, more particularly, adjustable cut guides for resecting the end of a bone.

Orthopedic procedures for the replacement of all, or a portion of, a patient's joint typically require resecting (cutting) and reshaping of the bones of the joint. For instance, total knee replacement procedures typically involve resecting the distal end of the femur and the proximal end of the tibia prior to implanting the prosthesis components. Resecting the distal end of the femur often involves making several cuts of the distal end of the femur including a distal cut, an anterior cut, a posterior cut, an anterior chamfer cut, and a posterior chamfer cut. The depth, angle and position of these cuts may depend on a variety of factors including the size of the prosthetic component, size of the patient's knee, and conditions of the patient's bone. In addition, the presentation of the patient's knee may indicate the need for adjustments for varus, valgus, flexion, extension, and rotation of the knee. Such adjustments may also affect the depth, angle and position of the cuts.

Cut guides have been developed to guide the saw and achieve the proper angle and position of these cuts. Conventional cut guides are often in the form of blocks having permanently positioned slots therein for receiving and guiding the saw. Different sized cut guide blocks are provided to correspond to different sized prostheses and to achieve the different cuts. In addition, some cut guide blocks require additional cut accessories to be mounted thereon to provide additional necessary guide slots. Accordingly, making the necessary cuts of the distal end of the femur may require the installation and assembly of multiple cut guide blocks and accessories. In addition, the location and angle of the slots cannot be adjusted once the block is mounted on the femur. Accordingly, it may be challenging to make adjustments in the depth, angle and position of the cuts for varus, valgus, flexion, extension, and rotation of the knee There is a need for an adjustable cut guide that can be used to guide a saw in making the distal, anterior, posterior and chamfer cuts.

SUMMARY

The present invention provides a multi-positionable cut guide for resecting the end of a bone. The cut guide is capable of being adjusted to guide multiple cuts of the end of the bone. In one form, the multi-positionable cut guide includes a bone attachment device, a base, and a guide member. The bone attachment device is adapted to be coupled to the bone and has a base receiving portion. The base includes a mounting portion slideably coupled to the base receiving portion of the attachment device such that the base is slideable relative to the attachment device along at least one dimension. The guide housing is pivotally mounted to the base, and the guide member is rotatably mounted to the guide housing. The guide member defines an axis about which it is rotatable. The guide member also includes an elongated guide slot extending along the axis and adapted to receive and guide a saw for resecting the end of the bone. The guide slot defines a cut guide plane, the position of which is adjustable relative to the bone via the sliding of the base along the at least one dimension, the pivoting of the guide housing relative to the base, and the rotation of the guide member about the axis.

In one aspect, either the base receiving portion or the mounting portion includes at least one groove. The other of base receiving portion and mounting portion includes a tongue complementary in shape to the groove such that the tongue is slideably disposed within the groove. In a further aspect, the at least one groove includes a first groove and a second groove. The first groove is perpendicular to the second groove and the tongue may be slideably coupled to either of first and second grooves such that the at least one dimension includes a first dimension and a second dimension. The base is slideable along the first dimension when the tongue is disposed within the first groove, and the base is slideable along the second dimension when the tongue is disposed within the second groove.

The cut guide of the present invention provides the ability to adjust the depth and angle of the anterior, posterior, distal and chamfer cuts to an infinite number of positions. The cut guide of the present invention, thereby, provides the user flexibility in making adjustments for varus, valgus, flexion, extension, and rotation of the knee.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
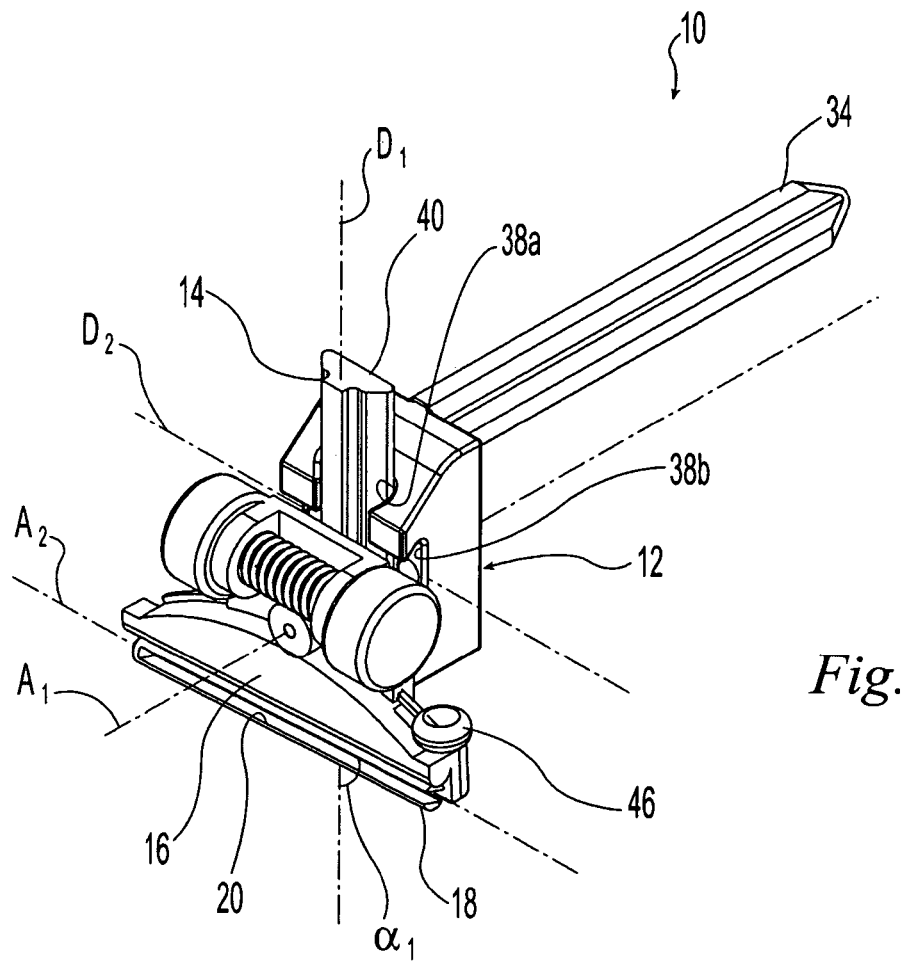
FIG. 1 is a perspective view of a cut guide according to one embodiment of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

The present invention will now be described with reference to the attached figures. The description below may include reference to the following terms: anterior (at or near the front of the body, as opposed to the back of the body); posterior (at or near the back of the body, as opposed to the front of the body); lateral (at or near the left or right side of the body, farther from the midsagittal plane, as opposed to medial); medial (in the middle, at or near the midsagittal plane, as opposed to lateral); proximal (toward the beginning, as opposed to distal); and distal (farther from the beginning, as opposed to proximal).

Referring to FIG. 1, cut guide 10 according to one embodiment of the present invention is illustrated. Cut guide 10 generally includes bone attachment device 12, base 14, guide housing 16 and guide member 18.

Figure 2:
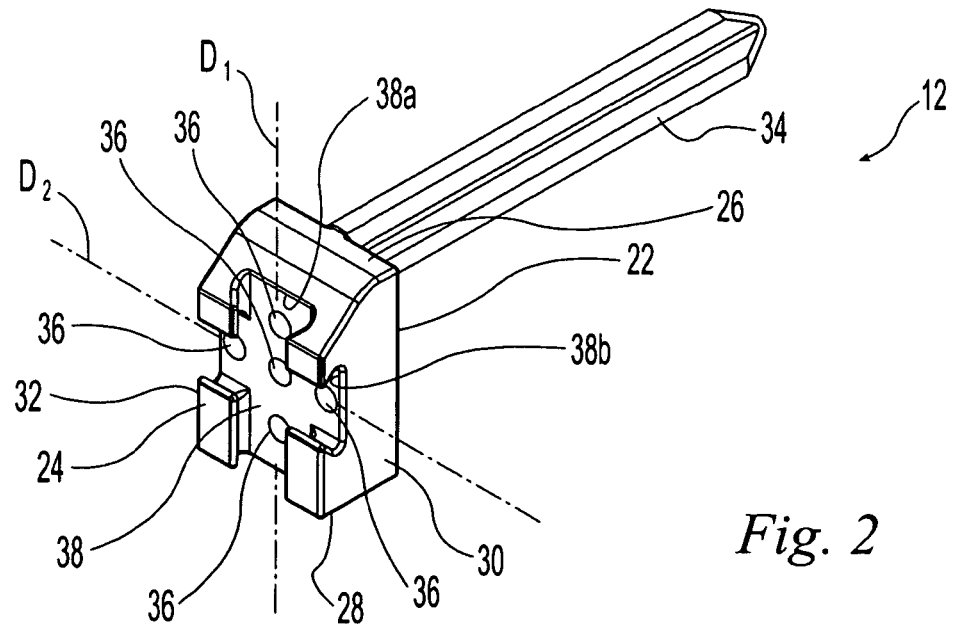
FIG. 2 is a first perspective view of the bone attachment device of the cut guide of FIG. 1.
Figure 3:
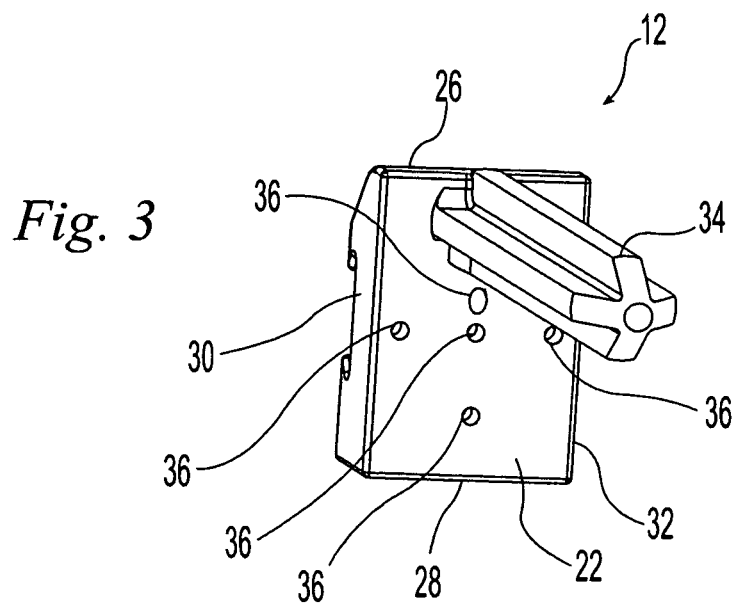
FIG. 3 is a second perspective view of the bone attachment device of FIG. 2.
Figure 7:
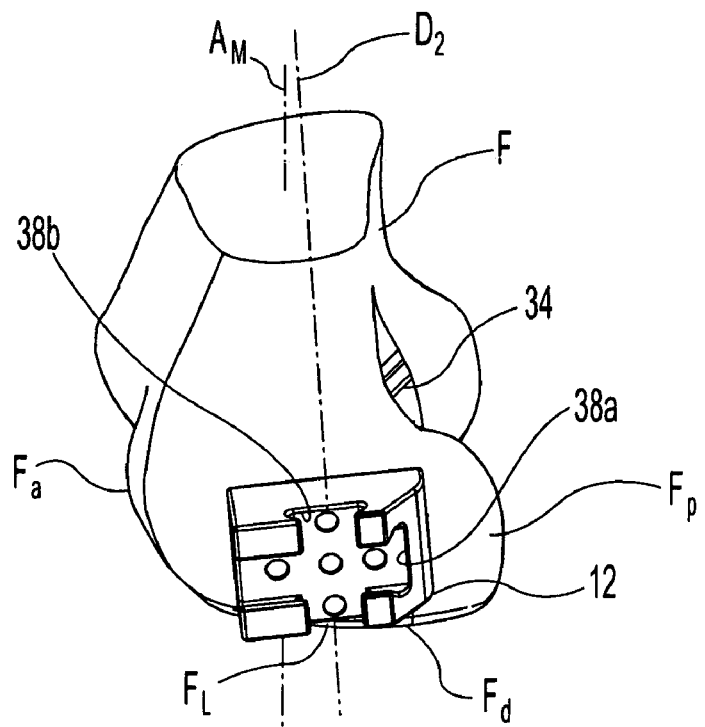
FIG. 7 is a lateral aspect of the distal end of a femur with the attachment device of FIG. 2 mounted thereon.

Turning to FIGS. 1-3, bone attachment device 12 includes bone engaging surface 22 and opposing exterior surface 24. Bone attachment device 12 is further defined by opposing first and second ends 26, 28 and opposing first and second sides 30, 32, each of which extends between bone engaging surface 22 and exterior surface 24. Bone attachment device 12 is adapted to be coupled to a bone, such as femur F, as illustrated in FIG. 7 and discussed in further detail below. To that end, bone attachment device 12 includes spike 34, as illustrated in FIGS. 1-3. Spike 34 may be driven into a pre-drilled hole in the bone as is discussed further below. Spike 34 has a cross-shaped cross section to aid in anchoring spike 34 in the bone and to prevent rotation of spike 34 in the bone. It should be understood that spike 34 may have different cross-sectional shapes including circular, rectangular and fluted shapes. Furthermore, bone attachment device 12 may include alternative or additional features for coupling bone attachment device 12 to the bone. For example, bone attachment device 12 may incorporate mounting screws, clamps or plates. For instance, bone attachment device 12 includes fastener receiving holes 36. Fastener receiving holes 36 are configured to receive fasteners (not shown) such as screws, pins or nails, which may extend through holes 36 and into the bone to secure bone attachment device 12 to the bone. Fastener receiving holes 36 may be an addition to, or an alternative for, spike 34.

Referring now to FIGS. 1 and 2, bone attachment device 12 also includes base receiving portion 38. Base receiving portion 38 includes first groove 38a and second groove 38b, each defined in exterior surface 24 of bone attachment device 12. First groove 38a extends longitudinally between first and second ends 26, 28 and along line or dimension $D_1$. Second groove 38b extends longitudinally along second dimension $D_2$ and between first and second sides 30, 32. Dimension $D_1$ is perpendicular to second dimension $D_2$ such that first and second grooves 38a, 38b are perpendicular to one another.

Figure 4:
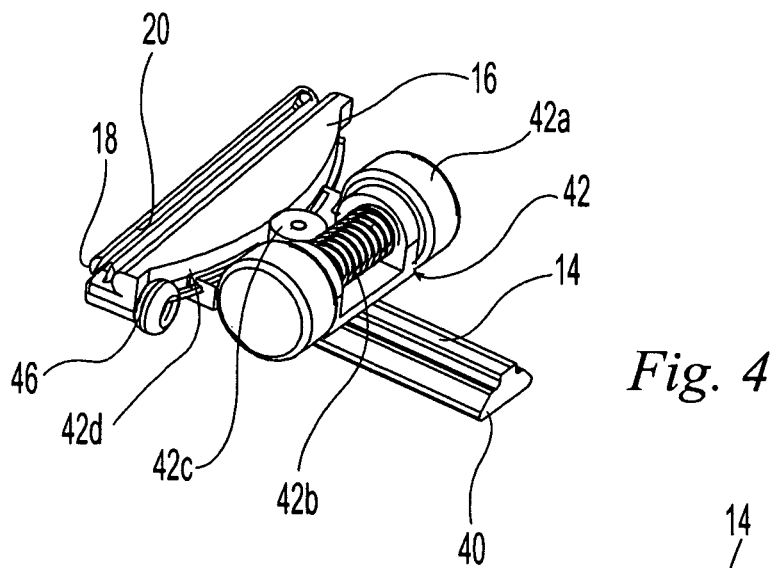
FIG. 4 is a perspective view of the cut guide of FIG. 1 wherein the bone attachment device has been removed.
Figure 5:
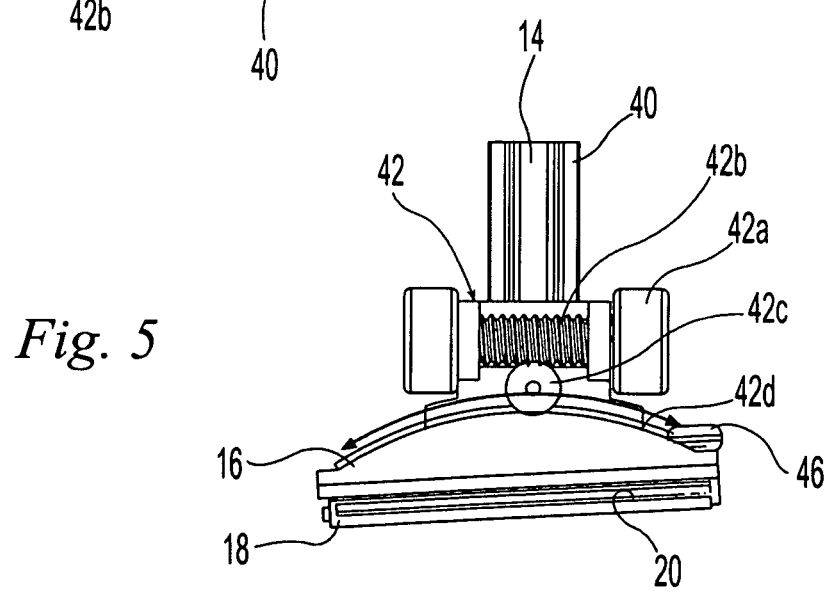
FIG. 5 is a top view of the cut guide of FIG. 4.

Turning now to FIGS. 1, 4 and 5, base 14 includes mounting portion 40. Mounting portion 40 has a shape complementary to first and second grooves 38a, 38b and is adapted to slide within first and second grooves 38a, 38b to slideably couple base 14 to bone attachment device 12. More particularly, as illustrated in FIGS. 2 and 4, first and second grooves 38a, 38b are in the form of dove tail-shaped grooves, while mounting portion 40 of base 14 is in the form of a dove tail-shaped tongue. Mounting portion 40 slideably fits within either of grooves 38a, 38b. It should be understood that mounting portion 40 and first and second grooves 38a, 38b may have any shape suitable to slideably secure base 14 to bone attachment device 12.

Referring back to FIGS. 1, 4 and 5, guide housing 16 is pivotally coupled to base 14 via guide housing adjustment device 42. Guide housing adjustment device 42 may be any mechanism adapted to pivot, swivel or turn housing 16 relative to base 14. For example, as illustrated in FIGS. 1, 4 and 5, adjustment device 42 may be a worm gear-type mechanism including actuator or knob 42a, threaded drive 42b and gear 42c. Knob 42a is coupled to threaded drive 42b such that rotation of knob 42a affects the rotation of threaded drive 42b. The threads of threaded drive 42b engage gear 42c such that the rotation of threaded drive 42b affects the rotation of gear 42c about housing axis $A_1$. Although not shown, gear 42c may be a toothed gear, the teeth of which engage the threads of threaded drive 42b. Gear 42c engages gear surface 42d of guide housing 16, such that the rotation of gear 42c about axis $A_1$ affects the swiveling of housing 16 as indicated by the double ended arrow. Gear surface 42d may have teeth (not shown) for engagement with gear 42c.

Figure 6:
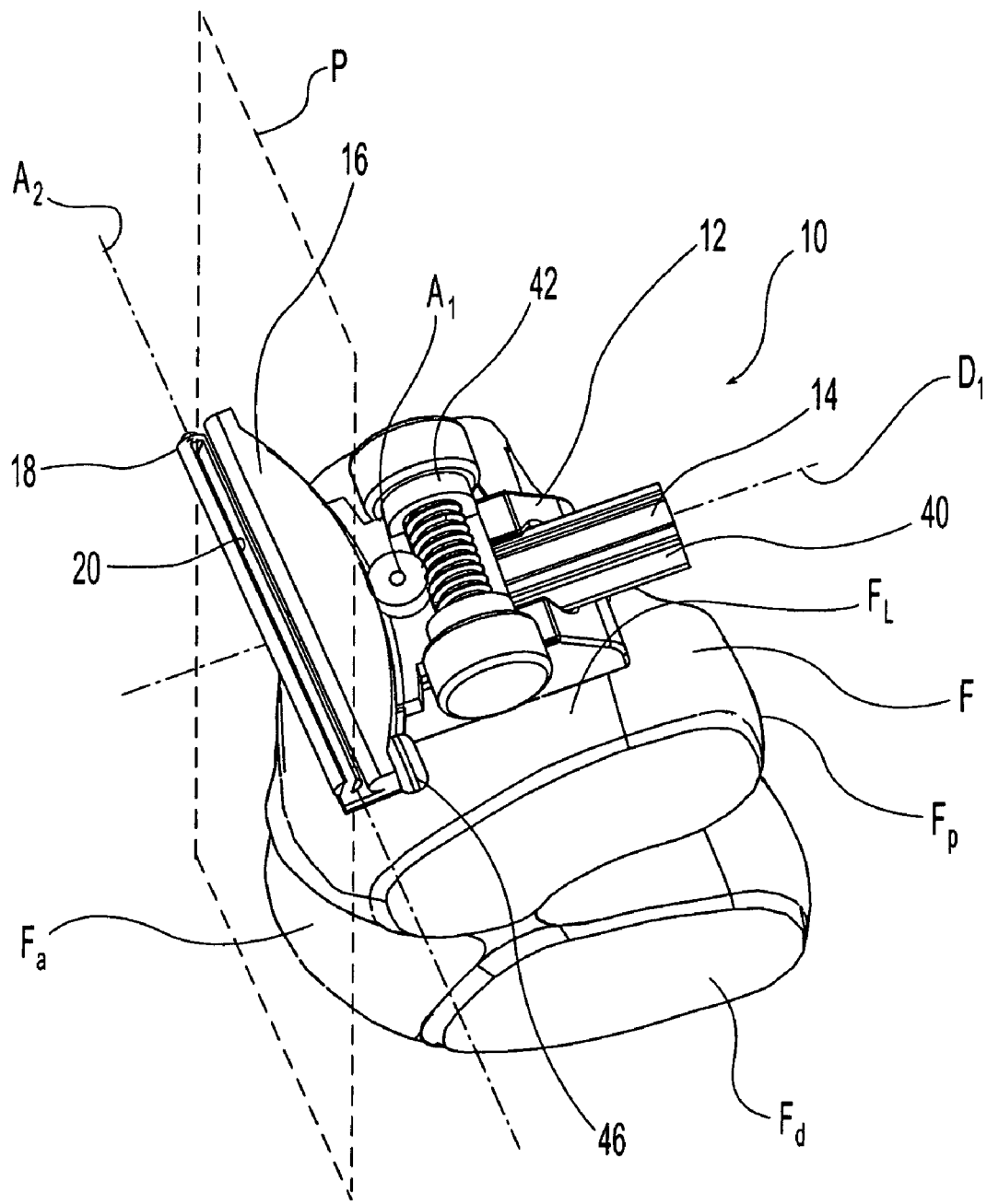
FIG. 6 is a lateral-distal perspective view of the distal end of a femur with the cut guide of FIG. 1 mounted thereon.

Referring still to FIGS. 1, 4 and 5, guide member 18 is rotatably coupled to housing 16. Guide member 18 is cylindrical in shape and defines guide axis $A_2$. It should be understood that guide member 18 need not be cylindrical in shape. For instance, guide member may be a substantially flat, rectangular paddle pivotally connected to housing 16 at guide axis $A_2$. Guide member 18 includes elongated slot 20 extending through guide member 18 along guide axis $A_2$. Guide slot 20 is adapted to receive and guide a saw (not shown). As shown in FIG. 6, guide slot 20 defines cut guide plane P along which the saw will cut when extending through guide slot 20.

Referring back to FIGS. 1, 4 and 5, cut guide 10 may include guide member adjustment device 46 operably engaged to guide member 18 and adapted to rotate or pivot guide member 18 about guide axis $A_2$. Guide member adjustment device 46 may be in any form capable of affecting the rotation of guide member 18. For instance, adjustment device 46 may be in the form of a worm gear mechanism (not shown). Such a mechanism might include a knob at one end and a threaded portion at the other end. The threaded portion would engage a gear (not shown) defined on the end of guide member 18. Rotation of the knob would induce the rotation of the threaded portion which, in turn, would cause the rotation of the gear of guide member 18. Alternatively, adjustment device may be in the form of a bevel gear mechanism or pivoting lever.

Referring now to FIGS. 6-10B, the operation of cut guide 10 will now be described with reference to its use in preparing the distal end of a femur. It should be understood, however, that the cut guide of the present invention may be adapted for use in preparing bones other than the distal end of the femur. As illustrated in FIGS. 6 and 7, femur F includes distal end $F_d$, posterior side $F_p$, anterior side $F_a$, medial side (not indicated) and lateral side $F_L$. Femur F defines mechanical axis $A_M$, commonly defined as a line drawn from the center of the femoral head (not shown) to the anterior/posterior (A/P) axis of the distal end of femur F. The A/P axis (not shown) is a line extending anterior to posterior across the distal end of the femur midway between the two condyles.

First, bone attachment device 12 is attached to lateral side $F_L$ of femur F. This may be accomplished by drilling a hole into lateral side $F_L$ of femur F and then driving spike 34 into the pre-drilled hole. As noted above, attachment device 12 may include features alternative to, or in addition to, spike 34 for attaching bone attachment device 12 to femur F. Bone attachment device 12 is coupled to and positioned on femur F such that second dimension $D_2$ of second groove 38b is nearly parallel with mechanical axis $A_M$ of femur F. As will be demonstrated in the discussion below, cut guide 10 is capable of adjusting the position of guide slot 20 relative to multiple aspects and to an infinite number of positions. As such, second dimension $D_2$ need not be aligned perfectly parallel with mechanical axis $A_M$.

Next, base 14 is coupled to bone attachment device 12 by sliding dove-tailed mounting portion 40 into one of first and second grooves 38a, 38b. Assuming that the distal end $F_d$ of femur F will be cut first, mounting portion 40 is slid into second groove 38b such that guide member 18 is positioned adjacent distal end $F_d$ of femur F, as shown in FIG. 8.

Figure 8:
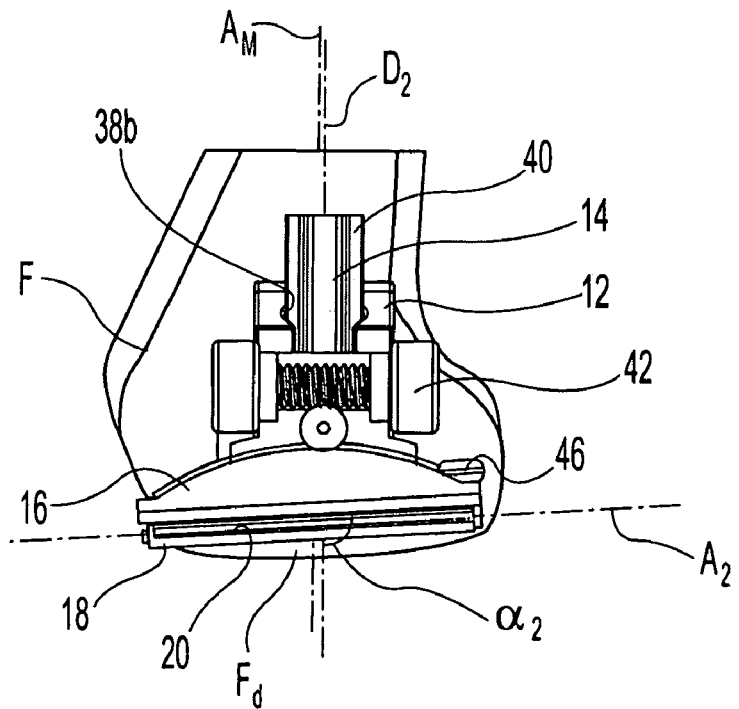
FIG. 8 is a lateral aspect of the distal end of a femur with the cut guide of FIG. 1 mounted thereon and wherein the cut guide is positioned to guide the distal cut.

Referring still to FIG. 8, the guide slot 20 is then adjusted to achieve the desired cut depth and angle. The position of guide slot 20 and, thus, cut plane P (FIG. 6) is adjustable relative to three aspects. First, the depth of the cut may be adjusted by sliding mounting portion 40 within second groove 38b such that the position of guide slot 20 and cut plane P translates along second dimension $D_2$. Second, the slope of cut guide plane P in an anterior to posterior direction may be adjusted by pivoting housing 16 about housing axis $A_1$. This pivoting movement of housing 16 tilts or pivots guide slot 20 relative to second dimension $D_2$ such that an angle $\alpha_2$ formed between guide axis $A_2$ and dimension $D_2$ changes as housing 16 is pivoted. This pivoting motion may be achieved using adjustment device 42. More particularly, knob 42a is rotated which causes threaded drive 42b to rotate. Threaded drive 42b engages gear 42c causing gear 42c to rotate about housing axis $A_1$. Rotating gear 42c travels along gear surface 42d of housing 16 to thereby turn housing 16. Thirdly, guide member 18 may be rotated about guide axis $A_2$ to adjust the slope of cut guide plane P in a medial-lateral direction by activating guide member adjustment device 46. A saw (not shown) is inserted through guide slot 20 and a cut along cut guide plane P is made to remove a portion of distal end $F_d$ of femur F.

Figure 9A:
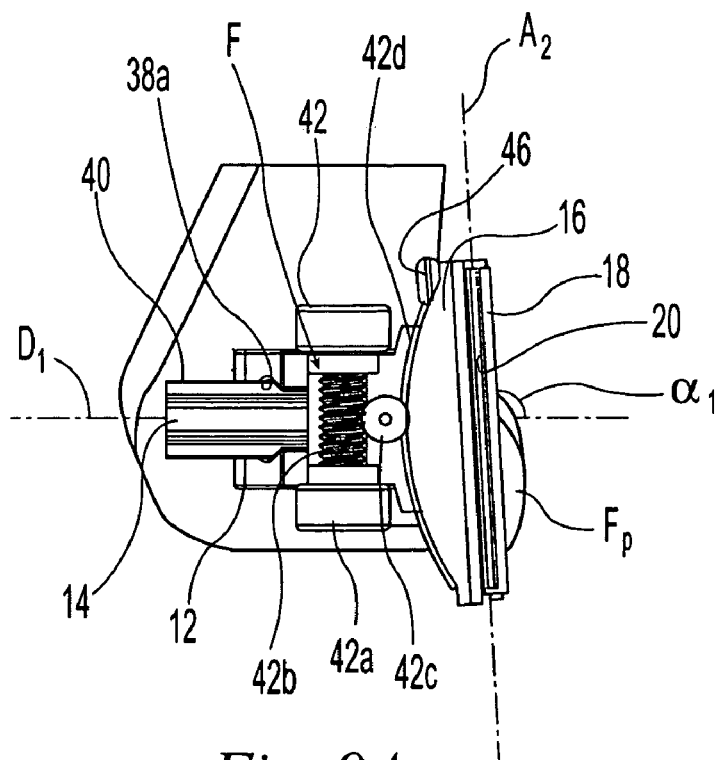
FIG. 9A is a lateral aspect of the femur and cut guide of FIG. 8 wherein the cut guide is positioned to guide the posterior cut.

Turning now to FIG. 9A, posterior side $F_p$ of femur F is cut by first sliding mounting portion 40 of base 14 from second groove 38b and sliding mounting portion 40 into first groove 38a at first end 26 of attachment device 12. Guide member 18 is now positioned adjacent posterior side $F_p$ of femur F. The depth of the posterior cut is adjusted by sliding mounting portion 40 within second groove 38a thereby adjusting the position of guide slot 20 along first dimension $D_1$. The slope of cut plane P in the distal to proximal direction may be adjusted by pivoting guide housing 16 and, thereby, adjusting angle $\alpha_1$ between guide axis $A_2$ and dimension $D_1$. Guide housing 16 may be pivoted, as described above, using housing adjustment device 42. The slope of cut plane P extending medial-laterally is adjusted by rotating guide member 18 about axis $A_2$, using guide member adjustment device 46. Once cut plane P is properly positioned, a saw (not shown) may be inserted through guide slot 20 to guide the posterior cut.

Figure 9B:
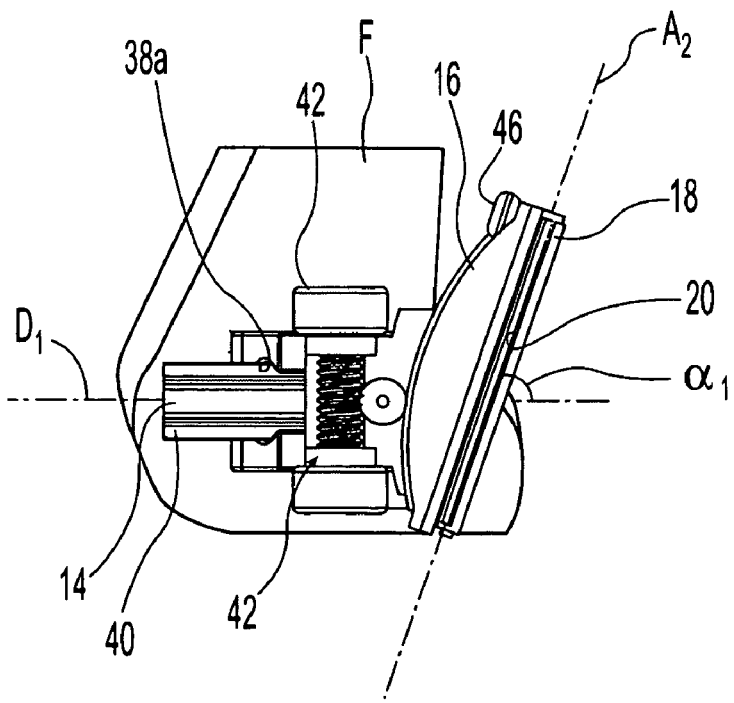
FIG. 9B is a lateral aspect of the femur and cut guide of FIG. 9A wherein the cut guide is positioned to guide the posterior chamfer cut.

Referring now to FIG. 9B, if chamfer cuts are needed, housing 16 is pivoted to thereby adjust angle $\alpha_1$ until the distal-proximal slope of cut plane P is in position to guide the posterior chamfer cut. A saw is then inserted through guide slot 20 to guide the posterior chamfer cut.

Figure 10A:
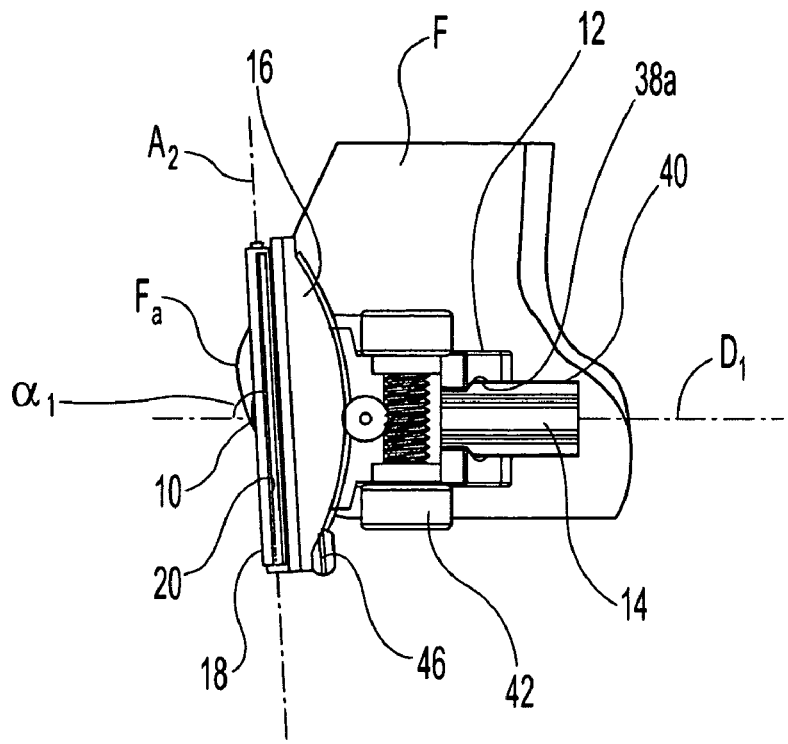
FIG. 10A is a lateral aspect of the femur and cut guide of FIG. 8 wherein the cut guide is positioned to guide the anterior cut.

Referring now to FIG. 10A, to remove a portion of anterior side $F_a$ of femur F, mounting portion 40 is slidingly removed from first groove 38a and re-inserted into first groove 38a from second end 28 of bone attachment device 12, such that guide member 18 is positioned adjacent anterior side $F_a$ of femur F. The adjustment steps described above with respect to the posterior cut are repeated to achieve the proper depth, medial-lateral slope and proximal-distal slope of cut guide plane P. Once cut plane P is positioned, the cut of the anterior side $F_a$ of femur F is made by inserting a saw through guide slot 20.

Figure 10B:
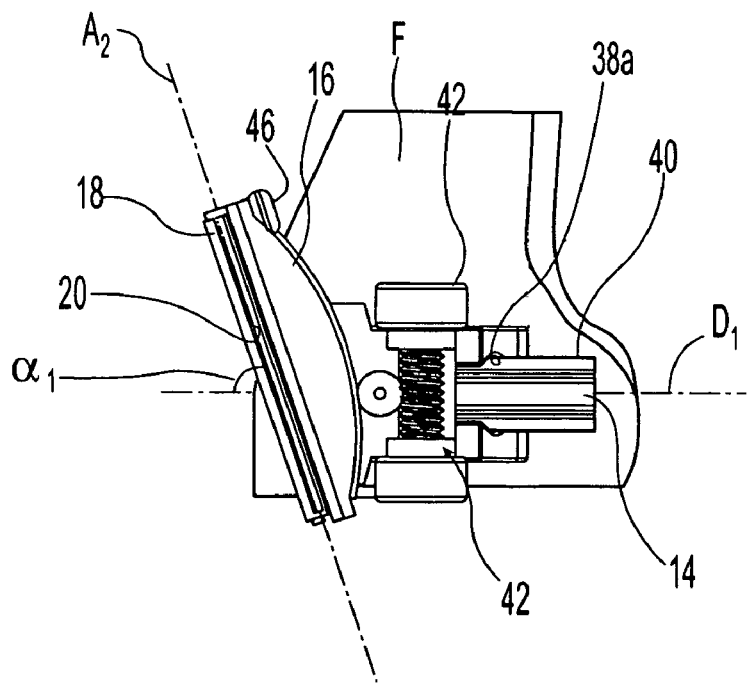
FIG. 10B is a lateral aspect of the femur and cut guide of FIG. 8 wherein the cut guide is positioned to guide the anterior chamfer cut.

Referring now to FIG. 10B, if chamfer cuts are needed, housing 16 is pivoted to thereby adjust angle $\alpha_1$ until the distal-proximal slope of cut plane P is in position to guide the posterior chamfer cut. A saw is then inserted through guide slot 20 to guide the anterior chamfer cut. Once the distal, posterior, anterior and chamfer cuts are made, cut guide 10 is removed from femur F by pulling spike 34 from femur F.

As demonstrated above, the cut guide of the present invention provides the ability to infinitely adjust the depth and angle of the anterior, posterior, distal and chamfer cuts, thereby allowing the user flexibility in making adjustments for varus, valgus, flexion, extension, and rotation of the knee.

Although use of cut guide 10 is described above as a lateral approach wherein cut guide 10 is mounted on the lateral side of femur F, cut guide 10 may be used alternatively in a medial approach wherein cut guide 10 is mounted on the medial side of the femur. Cut guide 10 may also be adapted to mount on the distal end of the femur to make the anterior, posterior and chamfer cuts. In this case, the cut guide may be adapted to mount on an IM rod. In addition, cut guide 10 described above illustrates base receiving portion 38 as being grooves and mounting portion 40 as being a complementary tongue. Alternatively, the cut guide could be adapted such that the base receiving portion on the bone attachment device includes the tongue, while the mounting portion on the base includes the grooves.

Cut guide 10 may be formed of any surgical grade rigid material such as stainless steel. The components of cut guide 10, particularly bone attachment device 12, base 14, guide housing 16 and guide member 18 may be formed of the same material or differing materials.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A multi-positionable cut guide for resecting an end of a bone, said cut guide comprising:
   a bone attachment device adapted to be coupled to the bone, said attachment device having a base receiving portion;
   a base having a mounting portion, said mounting portion slideably coupled to said base receiving portion of said attachment device such that said base is slideable relative to said attachment device along at least one dimension, wherein one of said base receiving portion and said mounting portion includes a first groove and a second groove, said first groove being perpendicular to said second groove, and wherein the other of said base receiving portion and said mounting portion is a tongue complementary in shape to said groove such that said tongue is slideably disposed within said groove, said tongue slideably coupled to either of said first and second grooves such that said at least one dimension includes a first dimension and a second dimension, said base being slideable along said first dimension when said tongue is disposed within said first groove and said base being slideable along said second dimension when said tongue is disposed within said second groove;

a guide housing pivotally mounted to said base about a first axis;

a guide member rotatably mounted to said guide housing, said guide member defining a second axis about which said guide member is rotatable relative to said guide housing, said guide member defining an elongated guide slot extending along said second axis and adapted to receive and guide a saw for resecting the end of the bone, said guide slot defining a cut guide plane, wherein a position of said cut guide plane relative to said bone is adjustable via the sliding of said base along said at least one dimension, the pivoting of said guide housing relative to said base about said first axis, and the rotation of said guide member about said second axis.

2. A multi-positionable cut guide for resecting an end of a bone, said cut guide comprising:

a bone attachment device adapted to be coupled to the bone, said attachment device having a base receiving portion, said base receiving portion including a first elongate groove and a second elongate groove, said second groove extending perpendicular to said first groove;

a base having a mounting portion, said mounting portion including a tongue, said tongue removably and slideably coupled to either one of said first or second grooves such that said base is slideable relative to said attachment device along a first dimension when said tongue is coupled to said first groove and said base is slideable relative to said attachment device along a second dimension when said tongue is couple to said second groove;

a guide housing pivotally mounted to said base;

a guide member mounted to said guide housing, said guide member defining an axis and including an elongated guide slot extending along said axis, said guide slot adapted to receive and guide a saw for resecting the end of the bone, said guide slot defining a cut guide plane, wherein a position of said cut guide plane relative to the end of the bone is adjustable in a first aspect by sliding said base along either one of said first and second dimensions, said position of said cut guide plane is adjustable in a second aspect by pivoting said guide housing relative to said base, and said position of said cut guide is adjustable in a third aspect by rotating said guide member about said axis.

3. The cut guide of claim 2 wherein said bone attachment device includes a spike adapted to be driven into the bone.

4. The cut guide of claim 2 wherein said bone attachment device includes at least one fastener opening, each of said at least one openings adapted to receive a fastener for securing said bone attachment device to the bone.

5. The cut guide of claim 2 further including a guide housing adjustment device, said guide housing adjustment device adapted to pivot said guide housing relative to said base.

6. The cut guide of claim 5 wherein said adjustment device is a worm gear apparatus.

7. The cut guide of claim 2 further including a guide member adjustment device, said guide member adjustment device adapted to rotate said guide member about said axis.

8. A multi-positionable cut guide for resecting an end of a bone, said cut guide comprising:

a bone attachment device adapted to be coupled to the bone, said attachment device having a base receiving portion;

a base having a mounting portion, said mounting portion slideably coupled to said base receiving portion of said attachment device such that said base is slideable relative to said attachment device along at least one dimension, wherein one of said base receiving portion and said mounting portion includes a first groove and a second groove, said first groove being perpendicular to said second groove, and wherein the other of said base receiving portion and said mounting portion is a tongue complementary in shape to said groove such that said tongue is slideably disposed within said groove, said tongue slideably coupled to either of said first and second grooves such that said at least one dimension includes a first dimension and a second dimension, said base being slideable along said first dimension when said tongue is coupled to said first groove and said base being slideable along said second dimension when said tongue is coupled to said second groove;

a guide housing mounted to said base;

a guide member mounted to said guide housing, said guide member defining an guide axis about which said guide member is rotatable relative to said guide housing, said guide member defining an elongated guide slot extending along said guide axis and adapted to receive and guide a saw for resecting the end of the bone, said guide slot defining a cut guide plane, wherein a position of said cut guide plane relative to said bone is adjustable relative to said at least one dimension and said guide axis.

9. The cut guide of claim 8 wherein each of said first and second dimensions are perpendicular to said housing axis.

10. A multi-positionable cut guide for resecting an end of a bone, said cut guide comprising:

a bone attachment device adapted to be coupled to the bone, said attachment device having a base receiving portion and a spike adapted to be driven into the bone;

a base having a mounting portion, said mounting portion slideably coupled to said base receiving portion of said attachment device such that said base is slideable relative to said attachment device along at least one dimension;

a guide housing mounted to said base;

a guide member mounted to said guide housing, said guide member defining an guide axis about which said guide member is rotatable relative to said guide housing, said guide member defining an elongated guide slot extending along said guide axis and adapted to receive and guide a saw for resecting the end of the bone, said guide slot defining a cut guide plane, wherein a position of said cut guide plane relative to said bone is adjustable relative to said at least one dimension and said guide axis.

11. A multi-positionable cut guide for resecting an end of a bone, said cut guide comprising:

a bone attachment device adapted to be coupled to the bone, said attachment device having a base receiving portion;

a base having a mounting portion, said mounting portion slideably coupled to said base receiving portion of said attachment device such that said base is slideable relative to said attachment device along at least one dimension;

a guide housing mounted to said base;

a guide member mounted to said guide housing, said guide member defining an guide axis about which said guide member is rotatable relative to said guide housing, said guide member defining an elongated guide slot extending along said guide axis and adapted to receive and guide a saw for resecting the end of the bone, said guide slot defining a cut guide plane, wherein a position of said cut guide plane relative to said bone is adjustable relative to said at least one dimension and said guide axis; and a guide housing adjustment device adapted to pivot said guide housing about a housing axis.

12. A multi-positionable cut guide for resecting an end of a bone, said cut guide comprising:

a bone attachment device adapted to be coupled to the bone, said attachment device having a base receiving portion;

a base having a mounting portion, said mounting portion slideably coupled to said base receiving portion of said attachment device such that said base is slideable relative to said attachment device along at least one dimension;

a guide housing mounted to said base;

a guide member mounted to said guide housing, said guide member defining an guide axis about which said guide member is rotatable relative to said guide housing, said guide member defining an elongated guide slot extending along said guide axis and adapted to receive and guide a saw for resecting the end of the bone, said guide slot defining a cut guide plane, wherein a position of said cut guide plane relative to said bone is adjustable relative to said at least one dimension and said guide axis; and a guide member adjustment device adapted to rotate said guide member about said guide axis.

* * * * *

UNITED STATES PATENT AND TRADEMARK OFFICE
CERTIFICATE OF CORRECTION

| | | |
|---|---|---|
| PATENT NO. | : 7,658,741 B2 | Page 1 of 1 |
| APPLICATION NO. | : 11/154774 | |
| DATED | : February 9, 2010 | |
| INVENTOR(S) | : Claypool et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this

Thirtieth Day of November, 2010

David J. Kappos
*Director of the United States Patent and Trademark Office*